United States Patent
Shi et al.

(10) Patent No.: US 11,761,002 B2
(45) Date of Patent: Sep. 19, 2023

(54) APPLICATION OF TRANSGENIC STEM CELL-DERIVED EXOSOME IN PREPARING MEDICAMENT OR WHITENING COSMETIC

(71) Applicant: GUANGDONG CELL BIOTECHNOLOGY CO., LTD., Dongguan (CN)

(72) Inventors: Xinyi Shi, Dongguan (CN); Taihua Wang, Dongguan (CN); Fei Peng, Dongguan (CN); Jing Li, Dongguan (CN)

(73) Assignee: GUANGDONG CELL BIOTECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 18/015,963

(22) PCT Filed: Mar. 22, 2021

(86) PCT No.: PCT/CN2021/082150
§ 371 (c)(1),
(2) Date: Jan. 13, 2023

(87) PCT Pub. No.: WO2022/016892
PCT Pub. Date: Jan. 27, 2022

(65) Prior Publication Data
US 2023/0193270 A1     Jun. 22, 2023

(30) Foreign Application Priority Data
Jul. 22, 2020  (CN) .................. 202010709851.9

(51) Int. Cl.
| C12N 15/113 | (2010.01) |
| A61P 17/00 | (2006.01) |
| A61P 35/00 | (2006.01) |
| A61K 8/14 | (2006.01) |
| A61K 8/60 | (2006.01) |
| A61K 8/98 | (2006.01) |
| A61K 9/127 | (2006.01) |
| A61K 35/36 | (2015.01) |
| A61Q 19/02 | (2006.01) |
| C12N 5/071 | (2010.01) |
| C12N 15/88 | (2006.01) |

(52) U.S. Cl.
CPC .............. *C12N 15/113* (2013.01); *A61K 8/14* (2013.01); *A61K 8/606* (2013.01); *A61K 8/985* (2013.01); *A61K 9/127* (2013.01); *A61K 35/36* (2013.01); *A61P 17/00* (2018.01); *A61P 35/00* (2018.01); *A61Q 19/02* (2013.01); *C12N 5/063* (2013.01); *C12N 15/88* (2013.01); *A61K 2800/86* (2013.01); *C12N 2310/141* (2013.01)

(58) Field of Classification Search
CPC .................. C12N 15/113; C12N 5/063; C12N 2310/141; A61K 8/606; A61K 35/36
See application file for complete search history.

(56) References Cited

FOREIGN PATENT DOCUMENTS

| CN | 107375944 A | 11/2017 |
| CN | 105483081 B | 9/2019 |
| WO | WO-2020030750 A1 * | 2/2020 ......... A61K 31/7105 |

OTHER PUBLICATIONS

Xing Zhichao, et al., Research progress of exosomes in melanoma, Modern Oncology, 2020, pp. 1777-1780, vol. 28, No. 10.
Anna Gajos-Michniewicz, et al., Role of miRNAs in Melanoma Metastasis, Cancers, 2019, pp. 1-23, vol. 326, No. 11.
Ting La, et al., A p53-Responsive miRNA Network Promotes Cancer Cell Quiescence, Cancer Research, 2018, pp. 6666-6679, vol. 78, No. 23.

* cited by examiner

*Primary Examiner* — Robert S Cabral
(74) *Attorney, Agent, or Firm* — Bayramoglu Law Offices LLC

(57) ABSTRACT

An application of a transgenic stem cell-derived exosome in preparing a medicament or whitening cosmetic is provided. In the present disclosure, miR-27b-3p is transfected into an epidermal stem cell, and a transgenic stem cell-derived exosome is harvested. It is experimentally verified that the exosome can inhibit the expression of PIK3R3 protein in melanocytes and the proliferation and migration of melanocytes; and safety experiments further demonstrate the safety of the exosome. Therefore, corresponding medicaments or cosmetics prepared from the exosome have excellent medicinal and cosmetic application prospects.

2 Claims, 2 Drawing Sheets
Specification includes a Sequence Listing.

APPLICATION OF TRANSGENIC STEM CELL-DERIVED EXOSOME IN PREPARING MEDICAMENT OR WHITENING COSMETIC

CROSS REFERENCE TO THE RELATED APPLICATIONS

This application is the national phase entry of International Application No. PCT/CN2021/082150, filed on Mar. 22, 2021, which is based upon and claims priority to Chinese Patent Application No. 202010709851.9, filed on Jul. 22, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJGY049_Sequence_Listing.txt, created on 01/10/2023, and is 1,567 bytes in size.

TECHNICAL FIELD

The present disclosure relates to the field of biology, in particular to an application of a transgenic stem cell-derived exosome in preparing a medicament or whitening cosmetic.

BACKGROUND

The secretion of exosomes is a universal cellular function. Exosomes are believed be composed of unique lipids and proteins, which can deliver various bioactive molecules, such as proteins, membrane receptors, mRNA, and microRNA, and participate in cell-to-cell communication, immune system regulation, and transport of genetic material.

In recent years, researchers have linked exosomes with skin diseases. It is found that exosomes are involved in skin physiological and pathological processes. For example, the exosomes can help regulate the secretion of proinflammatory cytokines in the skin microenvironment, promote angiogenesis and collagen deposition in skin defects, and regulate the proliferation and differentiation of skin fibroblasts. In addition, the exosomes also play a role in specific information transmission when the skin microenvironment changes, thereby promoting the occurrence of hypertrophic scars, skin sclerosis, cutaneous melanoma, and other skin diseases. Therefore, in the prevention and treatment of skin diseases, not only can exosomes be used as drug carriers to encapsulate drugs and selectively penetrate into lesions, such as inflammatory tissues or tumor sites, they can also be used as biomarkers for disease prediction and diagnose, or design drugs to block information transmission, so as to achieve the effect of preventing and treating skin diseases.

Chinese Patent CN105483081B provides a method for preparing exosomes secreted by umbilical cord mesenchymal stem cells (umsc-exosome) overexpressing microRNA145-5p and use thereof in various biological preparations that accelerate the healing of full-thickness skin defects while antagonizing cicatricial contracture. The exosomes are prepared by the following method: (1) subculture of human umbilical cord mesenchymal stem cells with a fresh umbilical cord; (2) preparation of mesenchymal stem cells overexpressing microRNA145-5p; (3) reserve of conditioned medium; and (4) extraction and purification of exosomes. The exosomes derived from human umbilical cord mesenchymal stem cells overexpressing microRNA145-5p can be used as a biological agent to transfer into a rat back full-thickness wound model, which can effectively promote skin granulation tissue proliferation, accelerate wound healing, and antagonize cicatricial contracture. However, this method cannot inhibit melanocyte proliferation.

Melanoma is a highly malignant tumor derived from melanocytes, and is a malignant tumor that originates from the embryonic neural crest. It is highly malignant and has a poor prognosis. Melanoma can occur in the skin, eyeballs, digestive tract, and reproductive system, but skin malignant melanoma is the most common. Because malignant melanoma is highly malignant and prone to early metastasis, even if radical surgery is performed early, the 5-year survival rate of the patient is less than 70%. Therefore, in recent years, people have turned their research direction to study the tumor microenvironment, explore the pathogenesis of melanoma, and find new breakthroughs from targeting immunotherapy.

It has been found that the transfer factor responsible for the recruitment of melanoma cells to the sentinel lymph node is upregulated by melanoma exosomes. The cell recruitment increased by melanoma exosomes and the gene expression of extracellular matrix and vascular growth factor can create a niche that is conducive to the recruitment, trapping and growth of melanoma cells in the sentinel lymph node microenvironment. Substantially, sentinel lymph node is the "soil" for melanoma metastasis, and melanoma exosomes act as "seeds". Wang Lei isolated, identified and stained the melanoma cell line B16-exosomes. Through fluorescence microscopy, Western blotting, cell proliferation assay, and cell migration assay, it is found that B16-exosomes can enter mesenchymal stromal cells (MSCs), significantly promote proliferation and migration capabilities thereof, and up-regulate the expression of α-SMA, and the activation of TGF-β receptor participates in the above changes. Therefore, in view of the characteristics of exosomes participating in the information transmission in the pathological process of melanoma, not only can exosomes be used as biomarkers for the diagnosis and prediction of patients with melanoma, but also drugs can be designed to block information transmission. For example, SB431542, a TGF-β receptor blocker, will hopefully control the pathological development of melanoma and develop new anti-tumor therapies on this basis.

In addition, a large number of miRNAs carried by exosomes can participate in cell-to-cell communication, and mRNAs that selectively target melanocytes can regulate the pigment status of melanocytes by changing gene expression and enzyme activity. It has been shown that miRNAs such as miR145, miR675, miR340, miR218, miR330-5p, miR211, miR-27a-3p, miR25, miR155, and miR-21a-5p affect the process of melanogenesis through a plurality of mechanisms.

Although there have been studies on the inhibition of melanocytes with exosomes derived from other cells, those on the inhibition of melanocytes with epidermal stem cell-derived exosomes are not enough. Because the epidermal stem cells of the skin have relatively active cell morphology, exosomes thereof have theoretically excellent effects on skin repair and assistance. Therefore, the selection of an epidermal stem cell as a research object requires vigorous development.

SUMMARY

An objective of the present disclosure is to provide a miR-27b-3p-overexpressing epidermal stem cell-derived exosome, a preparation method and use thereof.

The miR-27b-3p-overexpressing epidermal stem cell-derived exosome provided by the present disclosure efficiently targets melanin, inhibits cell growth and migration, and thereby inhibits tumor growth.

Further, a proven way that the miR-27b-3p-overexpressing epidermal stem cell-derived exosome can act on melanocytes is achieved by inhibiting the expression of PIK3R3 protein. Phosphoinositide-3-kinase regulatory subunit 3 (PIK3R3) is an important signal factor in signaling pathways, involved in a plurality of physiological processes including cell proliferation, growth, differentiation, cell migration, and apoptosis. Therefore, inhibiting the PIK3R3 protein can inhibit cell proliferation and migration.

The present disclosure provides a miR-27b-3p-overexpressing epidermal stem cell-derived exosome, and the miR-27b-3p-overexpressing epidermal stem cell-derived exosome is prepared according to the following steps:

step 1, transfecting miR-27b-3p into epidermal stem cells, and screening the epidermal stem cells for a miR-27b-3p-overexpressing epidermal stem cell; and step 2, culturing the miR-27b-3p-overexpressing epidermal stem cell obtained in step 1, collecting a supernatant, removing floating living cells by centrifugation to obtain an exosome-containing supernatant, and centrifuging the exosome-containing supernatant to obtain the miR-27b-3p-overexpressing epidermal stem cell-derived exosome.

The present disclosure further provides an application of the miR-27b-3p-overexpressing epidermal stem cell-derived exosome according to the above technical solution in preparing a medicament for treating melanoma.

The present disclosure further provides an application of the miR-27b-3p-overexpressing epidermal stem cell-derived exosome according to the above technical solution in preparing a cosmetic for whitening skin.

An application of the above exosome in preparing a medicament for treating melanoma is provided.

An application of the above exosome in preparing a whitening cosmetic is provided.

A pharmaceutical preparation is provided. The pharmaceutical preparation contains the above exosome and one or more pharmaceutically acceptable carriers or excipients and is prepared through a pharmaceutically acceptable preparation process.

A whitening cosmetic is provided, containing the above exosome and one or more cosmetic vehicles.

The present disclosure has the following beneficial effects:

In the present disclosure, miR-27b-3p is transfected into an epidermal stem cell, and a transgenic stem cell-derived exosome is harvested. It is experimentally verified that the exosome can inhibit the expression of PIK3R3 protein in melanocytes and the proliferation and migration of melanocytes; and safety experiments further demonstrate the safety of the exosome. Therefore, corresponding medicaments or cosmetics prepared from the exosome have excellent medicinal and cosmetic application prospects.

DETAILED DESCRIPTION OF THE EMBODIMENTS

Figure 1:
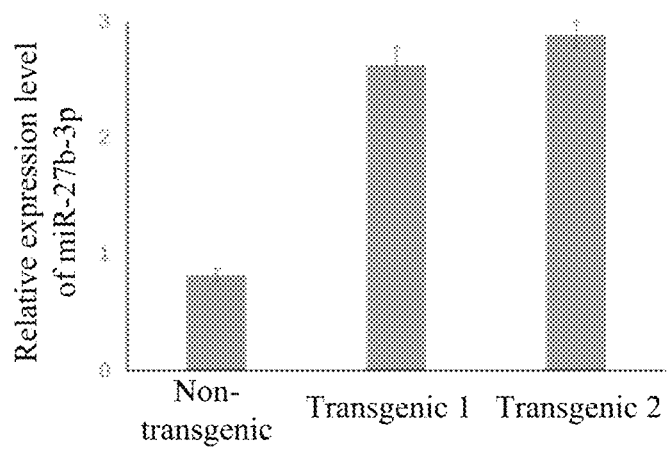
FIG. 1 illustrates the expression level of miR-27b-3p in stem cells.

The technical solutions provided by the present disclosure will be described below with reference to specific examples. All experimental materials that are not particularly emphasized in the following examples are conventional experimental materials, without special requirements, and they are all conventional materials easily obtained by those skilled in the art.

Example 1 Preparation of Human Epidermal Stem Cell-Derived Exosomes

1. Preparation of miR miR-27b-3p was 5'-uucacaguggcuaaguucugc-3' as shown in SEQ ID NO: 1; miR-27b-3p inhibitor was 5'-gcagaacuuagccacugugaa-3' as shown in SEQ ID NO: 2; and the nucleic acids were synthesized by Shanghai GenePharma Co., Ltd.

2. Cell Culture:

Human epidermal stem cells (purchased from BeNa Culture Collection, Cat #BNCC340781) were cultured in 10% fetal bovine serum (FBS)+90% high-sugar Dulbecco's Modified Eagle Medium (DMEM) at 37° C. in 5% $CO_2$. Well-grown epidermal stem cells were collected, centrifuged, counted, and plated in a 96-well plate at $5\times10^3$ cells per well, and cultured at 37° C. in 5% $CO_2$ for 24 h.

3. Transfection:

1) The day before transfection, the cultured cells were inoculated with a quantity of antibiotic-free medium in a 96-well plate, so that the cells reached 50% confluence during transfection;

2) the oligomer-Lipofectamine™ 2000 complex was prepared for transfection samples as follows:

a. miR-27b-3p, miR-27b-3p inhibitor, and negative control (nucleic acid-free Opti-MEM I medium) were diluted with 25 μL of serum-free Opti-MEM I medium (Gibco), respectively, and added into each well to obtain a final concentration of 50 nM, and mixed well gently, and three replicate wells were set up for each transfection;

b. Lipofectamine™ 2000 (Invitrogen) was mixed gently before use, 0.25 μL of which was diluted to 25 μL of Opti-MEM I medium, mixed well gently, and incubated at room temperature for 5 min; and c. after incubating for 5 min, the diluted Lipofectamine™ 2000 was mixed with the diluted nucleotides in step a and the control, respectively, mixed well gently, and incubated at room temperature for 20 min to allow the formation of complexes;

3) the complexes were added to each well containing cells and medium, and the culture plate was gently shaken back and forth to mix; the final concentration of nucleotides was 50 nM; and 4) the cells were further incubated in a 37° C., 5% $CO_2$ incubator for 72 h.

Example 2 Identification of Transgenic Epidermal Stem Cells

The expression of miR-27b-3p in transgenic epidermal stem cells was detected by RT-qPCR method. The well-grown cells prepared in Example 1 with 80% confluence were lysed with 1 mL of TRIzol and 200 μL of chloroform, the sample was shaken for 30 s and centrifuged at 14,000×g for 15 min at 4° C. to collect pellets; the pellets were dissolved in 60 μL DEPC water and extracted with equal volumes of phenol, chloroform and isopropanol, 1 μL of RNA was diluted 50-fold, and the absorbance (OD) value was measured on a microplate reader. For miR-27b-3p, the forward primer was ctcaactggtgtcgtggagt as shown in SEQ ID NO: 3, and the reverse primer was acactccagctgggtuucaca as shown in SEQ ID NO: 4; for internal reference U6, the forward primer was ctcgcttcggcagcaca as shown in SEQ ID NO: 5, and the reverse primer was aacgcttcacgaatttgcgt as shown in SEQ ID NO: 6; the experimental data were analyzed by the $2^{-\Delta\Delta CT}$ method, the expression of miR-27b-3p was detected, and two picked positive transgenic cells and control cells were tested. The results are shown in FIG. 1.

It can be seen from FIG. 1 that the expression level of miR-27b-3p in transgenic epidermal stem cells is nearly 3 times higher than that in non-transgenic epidermal stem cells, and the expression has been significantly upregulated. Therefore, the transgenic stem cells with the highest expression level of miR-27b-3p were selected for the subsequent preparation of exosomes.

Example 3 Preparation of Transgenic Stem Cell-Derived Exosomes

Figure 2:
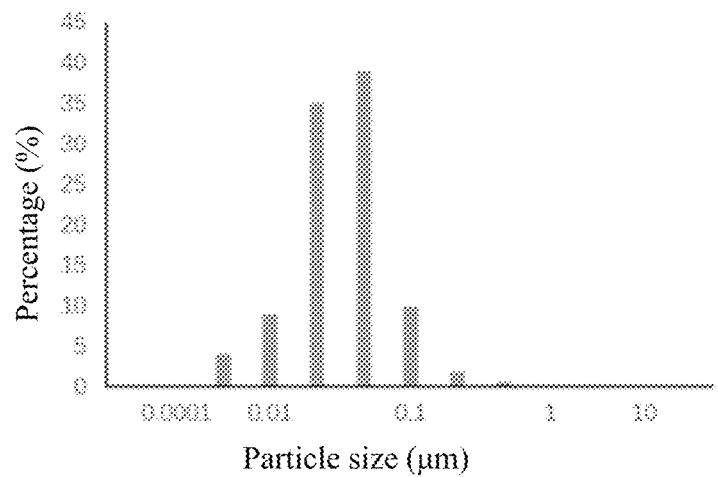
FIG. 2 illustrates the particle size distribution of stem cell-derived exosomes.

Collection of exosomes: When passage 3 cells grew until 80-90% confluence, the serum-free medium was changed, the cells were cultured for 48 h, and the cell supernatant was collected. The collected cell supernatant was centrifuged at 300×g for 10 min to remove dead cells and large cell debris, centrifuged at 2,000×g for 10 min to remove dead cells and cell debris, centrifuged at 10,000×g/min for 30 min to remove vesicles with large cell debris, and filtered through a 0.22 μm syringe filter to remove microbubbles and possible apoptotic bodies. The supernatant was transferred to an ultracentrifuge tube using a 20 mL empty syringe and centrifuged at $10^6$×g for 60 min, the supernatant was discarded, and pellets were collected to obtain crude exosomes. The crude exosomes were centrifuged at $10^6$×g for 60 min, the supernatant was discarded, and pellets were dissolved in 100 μL of phosphate-buffered saline (PBS) to obtain pure exosomes. The above operations were carried out at 4° C. under aseptic conditions. With 5 μL of exosome solution, the protein concentration of exosomes was determined by the bicinchoninic acid (BCA) assay. The determination result of the protein concentration of BCA was 1.72 g/L; one drop of exosomes was dropped on a copper mesh and negatively stained with 1% (v/v) phosphotungstic acid. After drying at room temperature, the shape of exosomes was observed and the diameter of exosomes was measured under a transmission electron microscope; 20 μL of exosome solution was diluted to 200 μL with PBS, and the diameter distribution was measured with a particle size analyzer. Exosomes were mostly elliptical in shape and had a membrane structure, with a diameter of (62.358±11.114) nm. The diameter of the exosomes identified by the particle size analyzer was concentrated in the range of 50-80 nm, as shown in FIG. 2. The exosomes were taken, and the expression level of miR-27b-3p was detected by the detection method of Example 2. It was found that the expression level in exosomes was substantially similar to that in the transgenic stem cells, and both were highly expressed.

Example 4 Cell Proliferation Assay

Figure 3:
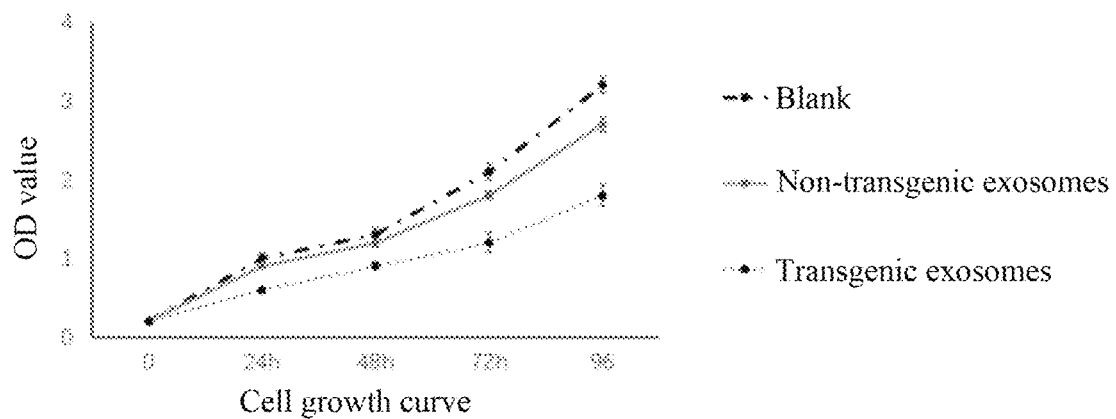
FIG. 3 illustrates cell proliferation assay results.

MU89 human melanocytes at logarithmic growth phase were taken, digested with 0.05% trypsin+0.53 mmol/L EDTA solution, and formulated into a cell suspension with a density of $6\times10^3$ cells/mL with fresh culture medium; the cell suspension was inoculated in a 96-well cell culture plate, 180 μL per well; each well was added with 50 μL each of transgenic and non-transgenic exosomes, respectively, a blank medium was used as a blank control, four sample mass concentration gradients were set for three samples, and each gradient was repeated three times. A 96-well plate was taken, the culture plate was incubated in a 37° C., 5% $CO_2$ conditional incubator for 0, 24, 48, 72, and 96 h, respectively, and 10 μL of CCK-8 solution was added to the well to be tested. Three samples were taken for each group of cells at each time point for testing, and the culture plate was incubated in the incubator. The absorbance at 450 nm was measured with a microplate reader. The results are shown in FIG. 3. CCK-8 assay shows that all exosomes can inhibit cell proliferation, but the transgenic exosomes have a better melanocyte inhibitory effect than non-transgenic exosomes.

Figure 4:
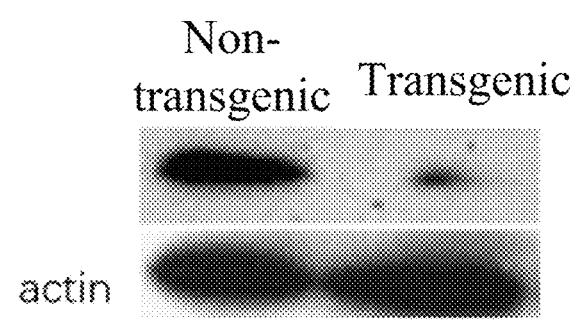
FIG. 4 illustrates Western blotting results.

Example 5 Detection of the Protein Expression Level of PIK3R3 by Western Blotting The protein was extracted from the melanocytes on which the aforementioned exosomes acted, run on 10% gel at 80 V for 90 min using the SDS-PAGE method, and electroblotted on a polyvinylidene fluoride (PVDF) membrane; after blocking, the blot was incubated with TBST primary antibody (goat anti-human PIK3R3 polyclonal antibody) overnight in a refrigerated incubator shaker at 4° C. After the membrane was washed, the blot was incubated with goat anti-rabbit IgG/horseradish peroxidase labeled secondary antibody for 2 h and exposed in a dark room. The exposed film was rinsed and dried for image acquisition. The results are shown in FIG. 4. After transgenic exosomes acted on melanocytes, the protein expression level of PIK3R3 in melanocytes was significantly inhibited. This indicates that the miR can act on PIK3R3 protein.

Example 6 Detection of the Migration Ability of Melanoma Cells by Transwell Invasion Assay Transwell chambers were placed in a 24-well plate, evenly applied with 50 of Matrigel (0.2 μg/μL) on the inner membrane of each Transwell chamber, and incubated at 37° C. for 15 min for gelling; after digestion, centrifugation, and cell counting, the cells were diluted with serum-free medium ($2.5\times10^4$ cells/mL) to prepare a cell suspension; the cell suspension (200 μL per well) was added to the upper Transwell chamber, while 600 μL of 10% FBS+culture medium was added to the lower Transwell chamber, and the Transwell chamber was incubated in the 37° C. incubator; the cells were fixed with formaldehyde and stained with crystal violet for 10 min, and the cells on the inner membrane were gently scraped with a cotton swab. Under a microscope, cells passing through the filter membrane were counted under four high-power fields (×40). The cells corresponded to: MU89 human melanocytes treated with transgenic exosomes, MU89 human melanocytes treated with non-transgenic exosomes, and pure MU89 human melanocytes, respectively. The assay was repeated three times. The ability of cells to invade through Matrigel can reflect the cell invasion ability. Transwell assay results are shown in Table 1 below.

TABLE 1

The ability of cells to invade through Matrigel

| Group | Number of cells passing through Matrigel |
| --- | --- |
| Transgenic exosomes | 32.90 ± 4.25 |
| Non-transgenic exosomes | 76.14 ± 6.51 |
| Blank control | 343.55 ± 25.19 |

As can be seen from Table 1: the number of MU89 human melanocytes treated with transgenic exosomes passing through Matrigel is (32.90±4.25), the number of MU89 human melanocytes treated with non-transgenic exosomes passing through Matrigel is (76.14±6.51), and the number of pure MU89 human melanocytes passing through Matrigel is (343.55±25.19). It can be seen that the ability of melanocytes treated with exosomes to pass through Matrigel has been significantly inhibited, and especially, the cells treated with transgenic exosomes have a stronger inhibiting ability.

Example 7 Inhibitory Activity of Exosomes Against Melanoma Xenograft in Nude Mice The experimental nude mice were acclimatized in independent ventilated cages for one week under specific pathogen-free (SPF) conditions. One week later, 0.1 mL of MU89 human melanocyte suspension (containing $5 \times 10^6$ cells in the logarithmic growth phase) was subcutaneously inoculated into the armpit of nude mice. When the tumor grew to a volume of about 100 mm$^3$ (for about 12 days), intraperitoneal administration proceeded in groups. The grouping was as follows: each group of 8 rats was administered by intraperitoneal injection for 14 days.

Control group: normal saline+1% dimethyl sulfoxide (DMSO).

Experimental group 1: transgenic exosomes group: 15 mg/(kg·day).

Experimental group 2: non-transgenic exosomes group: 15 mg/(kg·day).

Tumor inhibition rate (%)=(1−tumor volume in the exosome group/tumor volume in the control group)×100%. The data were expressed as mean±standard deviation. The data were processed by SPSS13.0 statistical software, and the significance of the differences between the groups was analyzed by one-way analysis of variance (ANOVA) of completely randomized design. P<0.05 was considered as statistically significant. Table 3 shows the tumor inhibition rate (%) of each group.

TABLE 1

Terminal xenograft tumor volume after exosome treatment (cm$^3$)

| | Terminal xenograft tumor volume (cm$^3$) | Tumor inhibition rate |
| --- | --- | --- |
| Control group | 1.88 ± 0.21 | / |
| Experimental group | 10.42 ± 0.11 | 77.66% |
| Experimental group | 20.92 ± 0.34 | 51.06% |

During the exosome intervention, there were no drug-induced deaths in the nude mice with xenograft tumor in each group. There was no statistically significant difference in the body mass of the nude mice with xenograft tumor in each group before the intervention, and there was also no statistical difference in the body mass of the nude mice with xenograft tumor in each group after the intervention. Compared with the control group, the tumor volume was significantly reduced in the transgenic exosomes group (P<0.05).

Example 8 Safety Experiment

Experimental Materials and Methods

Animals: White rabbits, general laboratory animals. The animals showed no abnormalities on physical examination.

Environmental conditions: room temperature: 22° C.-25° C., relative humidity: 60%-70%;

Experimental Method:

In accordance with the acute skin irritation test in the Hygienic Standard for Cosmetics (2007 edition) acute skin irritation test, 24 h before the test, the hair on both sides of the flank of the test animal was cut off, and the dehairing range was 3*3 cm. 0.5 mL of the tested exosomes were applied directly on the right skin, covered with a clean gauze, and fixed with non-irritating tape for 2 h. The other side served as a negative control. At 1, 24, 48, and 72 h after removing the test substance, the skin reaction of the contact part of the test animal was observed and recorded.

Conclusion:

Under the conditions of this test, the acute skin irritation test of white rabbits by exosomes is classified as non-irritating according to the intensity of skin irritation, which has excellent safety.

What is claimed is:

1. A method of making a medicament comprising a miR-27b-3p-overexpressing epidermal stem cell-derived exosome, wherein the miR-27b-3p-overexpressing epidermal stem cell-derived exosome is prepared according to the following steps:
   step 1, transfecting miR-27b-3p into epidermal stem cells, and screening the epidermal stem cells for amiR-27b-3p-overexpressing epidermal stem cell; and
   step 2, culturing the miR-27b-3p-overexpressing epidermal stem cell obtained in step 1, collecting a supernatant, removing floating living cells by a centrifugation to obtain an exosome-containing supernatant, and centrifuging the exosome-containing supernatant to obtain the miR-27b-3p-overexpressing epidermal stem cell-derived exosome;
   a transfection is achieved by an electroporation or a liposome-mediated transformation;
   a melanocyte is an MU89 human melanocyte.

2. A method of making a cosmetic comprising a miR-27b-3p-overexpressing epidermal stem cell-derived exosome, wherein the miR-27b-3p-overexpressing epidermal stem cell-derived exosome is prepared according to the following steps:
   step 1, transfecting miR-27b-3p into epidermal stem cells, and screening the epidermal stem cells for amiR-27b-3p-overexpressing epidermal stem cell; and
   step 2, culturing the miR-27b-3p-overexpressing epidermal stem cell obtained in step 1, collecting a supernatant, removing floating living cells by a centrifugation to obtain an exosome-containing supernatant, and centrifuging the exosome-containing supernatant to obtain the miR-27b-3p-overexpressing epidermal stem cell-derived exosome;
   a transfection is achieved by an electroporation or a liposome-mediated transformation;
   a melanocyte is an MU89 human melanocyte.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: The sequence is synthesized.

<400> SEQUENCE: 1
uucacagugg cuaaguucug c       21

<210> SEQ ID NO 2
<211> LENGTH: 21
<212> TYPE: DNA
<213> ORGANISM: Artificial Sequence
<220> FEATURE:
<223> OTHER INFORMATION: The sequence is synthesized.

```
<400> SEQUENCE: 2
gcagaacuua gccacuguga a                                              21

<210> SEQ ID NO 3
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 3
ctcaactggt gtcgtggagt                                                20

<210> SEQ ID NO 4
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 4
acactccagc tggguucaca                                                20

<210> SEQ ID NO 5
<211> LENGTH: 17
<212> TYPE: DNA
<213> ORGANISM: Artificial Sequence
<220> FEATURE:
<223> OTHER INFORMATION: The sequence is synthesized.

<400> SEQUENCE: 5
ctcgcttcgg cagcaca                                                   17

<210> SEQ ID NO 6
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 6
aacgcttcac gaatttgcgt                                                20
```